US008735168B2

(12) United States Patent
Ahlquist et al.

(10) Patent No.: US 8,735,168 B2
(45) Date of Patent: May 27, 2014

(54) REMOVING POLYPEPTIDES FROM STOOL (75) Inventors: David A. Ahlquist, Rochester, MN (US); Harold R. Bergen, Spring Valley, MN (US); Patrick S. Quint, Kasson, MN (US); Jonathan J. Harrington, Madison, WI (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 456 days.

(21) Appl. No.: 12/740,803

(22) PCT Filed: Nov. 21, 2008

(86) PCT No.: PCT/US2008/084278
§ 371 (c)(1),
(2), (4) Date: Jul. 13, 2010

(87) PCT Pub. No.: WO2009/067642
PCT Pub. Date: May 28, 2009

(65) Prior Publication Data
US 2012/0028367 A1 Feb. 2, 2012

Related U.S. Application Data (60) Provisional application No. 60/989,578, filed on Nov. 21, 2007.

(51) Int. Cl.
*G01N 1/40* (2006.01)

(52) U.S. Cl.
USPC .......................................... 436/178; 436/518

(58) Field of Classification Search
CPC ........... G01N 1/405; G01N 33/50; C01K 1/22
See application file for complete search history.

(56) References Cited

U.S. PATENT DOCUMENTS

2005/0095726 A1   5/2005   Fang

OTHER PUBLICATIONS

Jungblut, Peter R. et al. "Proteomics in human disease: Cancer, heart and infectious diseases," Chapter 5 of From Genome to Proteome: Advances in the Practice and Application of Proteomics. p. 52-62 (2000).*
Menard, S. et al. "Lactic acid bacteria secrete metabolites retaining anti-inflammatory properties after intestinal transport." Gut (2004) 53 821-828.*
Moritz, Robert L. et al. "Proteomic analysis of colorectal cancer: prefractionation strategies using twodimensional free-flow electrophoresis." Comparative and Functional Genomics (2005) 6 236-243.*
Perlmutter, David H. et al. "The alpha-1-Antitrypsin Gene is Expressed in a Human Intestinal Epithelial Cell Line." Journal of Biological Chemistry (1989) 264 9485-9490.*
Vanpoucke, H. et al. "Evaluation of six commercial assays for the rapid detection of *Clostridium difficile* toxin and/or antigen in stool specimens." Clinifcal Microbiology and Infection (2001) 7 55-64.*
Gronborg, Mads et al. "Comprehensive Proteomic Analysis of Human Pancreatic Juice." Journal of Proteome Research (2004) 3 1042-1055.*
MacFarlane, G. T. et al. "Starch utilization by the human large intestinal microflora." Journal of Applied Bacteriology (1986) 60 195-201.*
International Search Report dated Jul. 16, 2009, International Patent Application No. PCT/US2008/084278, International Filing Date Nov. 21, 2008.
Seam, L., et al., "Quality Control of Serum Albumin Depletion for Proteomic Analysis," Clinical Chemistry, Nov. 1, 2007, vol. 53, No. 11, pp. 1915-1920.
Huang, L., et al., "Digging Deeper and Faster Into Proteome by IgY-Immunoaffinity Fractionation," Journal of Biomolecular Techniques, Feb. 2007, vol. 19, pp. 10-11.
Huang, L., and Fang, X, "Immunoaffinity Fractionation of Plasma Proteins by Chicken IgY Antibodies," Methods Mol. Biol., Mar. 2008, vol. 425, pp. 41-51.
Kurasawa, et al., "Plant Residue and Bacteria as Bases for Increased Stool Weight Accompanying Consumption of Higher Dietary Fiber Diets," J. Am. Coll. Nutr., 19(4):426-433(2000).
Walsh and Terdiman, JAMA, "Colorectal Cancer Screening: Scientific Review," vol. 289, No. 10, pp. 1288-1296 (2003).
Bruger, J. Lab. Clin. Med., :"The detection of occult blood in feces including observations on the ingestion of iron and whole blood," 38(3): 433-45 (1951).
Jarnum and Peterson,"Protein-Losing Enteropathy," Lancet, 25(1): 417-21 (1961).
Aebersold and Mann, "Mass Spectrometry-Based Proteomics," Nature, 422:198-207 (2003).
McDonald and Yates, "Shotgun proteomics and biomarker discovery," Dis. Markers, 18:99-105 (2002).
Wilm, et al., "Femtomole sequencing of proteins from polyacrylamide gels by nano-electrospray mass spectrometry," Nature, 379:466-469 (1996).
Keller, et al., "Empirical Statistical Model to Estimate the Accuracy of Peptide Identifications Made by MS/MS and Database Search," Anal. Chem. 74(20): 5383-92 (2002).

(Continued)

*Primary Examiner* — Christopher A Hixson
(74) *Attorney, Agent, or Firm* — Casimir Jones SC (57) ABSTRACT

This document provides methods and materials involved in removing polypeptides (e.g., high abundance polypeptides) from stool samples. For example, methods and materials for preparing a stool sample for detecting polypeptides of low abundance are provided. For example, this document provides methods and materials for depleting abundant polypeptides common to stool from normal, healthy humans from a stool sample. Such depleted stool samples can be used to detect polypeptides of interest such as low abundance polypeptides or neoplasm-specific polypeptide markers that can be present in a mammal suffering from a disease such as cancer.

2 Claims, 5 Drawing Sheets (56) References Cited

OTHER PUBLICATIONS

Heppelmann, et al., "A simple method to remove contaminating salt from IPG strips prior to IEF," Electrophoresis, 28(21):3988-91 (2007).

Adkins, et al., "Toward a Human Blood Serum Proteome,"Mol. Cell. Proteomics, 1:947-955 (2002).

Bjorhall, et al., "Comparison of Different Depletion Strategies for Improved Resolution in Proteomic Analysis of Human Serum Samples," Proteomics, 5:1:307-317 (2004).

Kelleher, et al., "Top Down Versus Bottom Up Protein Characterization by Tandem High-Resolution Mass Spectrometry," J. Am. Chem. Soc., 121:806-812 (1999).

Merrell, et al., "Analysis of Low-Abundance, Low-Molecular-Weight Serum Proteins Using Mass Spectrometry," J. Biomol. Tech., 15:238-248 (2004).

Thadikkaran and Tissot, et al., "Recent Advances in Blood-Related Proteomics," Proteomics, 5:3019-3034 (2005).

Richter, et al., "Composition of the Peptide Fraction in Human Blood Plasma: Database of Circulating Human Peptides," J. Chromatogr. B. Biomed. Sci. Appl., 726:25-35 (1999).

Wolters, et al., "An Automated Multidimensional Protein Identification Technology for Shotgun Proteomics," Anal. Chem., 73:5683-5690 (2001).

Wu, et al. "Evaluation of Shotgun Sequencing for Proteomic Analysis of Human Plasma Using HPLC Coupled with Either Ion Trap or Fourier Transform Mass Spectrometry," J. Proteome Res., 2(4):383-93 (2003).

Nesvizhskii, Alexey I., et al., "A Statistical Model for Identifying Proteins by Tandem Mass Spectrometry," Anal. Chem. 2003, 75(17), pp. 4646-4658.

* cited by examiner

A)
1. Pancreatic alpha-amylase AMYP_HUMAN
2. Alpha-amylase 2B AMYC_HUMAN
3. Salivary alpha-amylase AMYS_HUMAN B)
1. Pancreatic alpha-amylase AMYP_HUMAN
2. Alpha-amylase 2B AMYC_HUMAN
3. Ig kappa chain C region KAC_HUMAN C)
1. Pancreatic alpha-amylase AMYP_HUMAN
2. Alpha-amylase 2B AMYC_HUMAN
3. Salivary alpha-amylase AMYS_HUMAN D)
1. Pancreatic alpha-amylase AMYP_HUMAN
2. Carboxypeptidase A1 CBPA1_HUMAN
3. Elastase-2A ELA2A_HUMAN

E)
1. Pancreatic alpha-amylase AMYP_HUMAN
2. Elastase-2A ELA2A_HUMAN
3. Maltase-glucoamylase, intestinal MGA_HUMAN F)
1. Pancreatic alpha-amylase AMYP_HUMAN
2. Elastase-2A ELA2A_HUMAN
3. Intestinal alkaline phosphatase PPBI_HUMAN

G)
1. Pancreatic alpha-amylase AMYP_HUMAN
2. Alpha-amylase 2B AMYC_HUMAN
3. Dipeptidyl peptidase 4 DPP4_HUMAN H)
1. Elastase-2A ELA2A_HUMAN
2. Pancreatic alpha-amylase AMYP_HUMAN
3. Intestinal alkaline phosphatase PPBI_HUMAN

REMOVING POLYPEPTIDES FROM STOOL

CROSS-REFERENCE TO RELATED APPLICATIONS

This application is a Section 371 U.S. National Stage entry of pending International Patent Application No. PCT/US2008/084278, international filing date, Nov. 21, 2008, which claims the benefit of expired U.S. Application Ser. No. 60/989,578, filed on Nov. 21, 2007.

BACKGROUND

1. Technical Field

This document relates to methods and materials involved in depleting polypeptides (e.g., high abundance polypeptides) from stool samples.

2. Background Information

Human stool is composed primarily of materials that are not digested or are not absorbed. Human stools are roughly 75 percent water and 25 percent solid matter (Kurasawa et al., *J. Am. Coll. Nutr.*, 19(4):426-433 (2000)). The solid matter, which makes up the fecal dry weight, includes roughly 30-50 percent bacteria, 30-40 percent undigestible food constituents such as cellulose and extra fibers, and variable amounts of organic wastes including fats.

The soluble, aqueous phase of stool is a diagnostically relevant constituent of stool from which can be derived pathologically important biomarkers. Several biochemical assays exist for the determination of colon disease, including measurement of fecal occult blood for the detection of colorectal cancer (Walsh and Terdiman, *JAMA*, 289:1288-1296 (2003) and Peranio and Bruger, *J. Lab. Clin. Med.*, 38(3):433-45 (1951)), an assay for the detection of protein loosing enteropathy (Jarnum and Peterson, Lancet, 25(1):417-21 (1961)), and assays designed to capture fecal DNA and determine its use in pathological diagnosis.

SUMMARY

This document relates to methods and materials involved in removing polypeptides (e.g., high abundance polypeptides) from stool samples. Removing polypeptides from a stool sample can reduce the complexity of the stool sample and can allow low abundance polypeptides to be more readily detected. For example, the removal of high abundance, host polypeptides from a stool sample can allow low abundance polypeptides to be detected in the pico, femto, or sub-femto molar range. In some cases, removing high abundance polypeptides can reduce the incidence of peptide ion suppression, which is a mass spectrometry phenomenon that can occur during co-elution and can mask the signals of low abundance polypeptides.

In general, one aspect of this document features a method for preparing a stool sample for detecting a low abundance polypeptide. The method comprises reducing the level of a predetermined polypeptide present in a stool sample. The predetermined polypeptide can be a human polypeptide. The predetermined polypeptide can be a bacterial polypeptide. The predetermined polypeptide can be abundant in human stool. The stool sample can be a human stool sample. The predetermined polypeptide can be a polypeptide set forth in Table 1 or 2. An antibody conjugated resin can be used to reduce the level of the predetermined polypeptide present in the stool sample. The antibody can be an IgY antibody.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document provides methods and materials related to removing polypeptides from stool. For example, this document provides methods and materials for depleting abundant polypeptides common to stool from normal, healthy humans from a stool sample. Such depleted stool samples can be used to detect polypeptides of interest such as low abundance polypeptides or neoplasm-specific polypeptide markers that can be present in a mammal suffering from a disease such as cancer. In some cases, a stool sample provided herein can be used to determine whether or not a mammal has a biomarker indicative of colon cancer or supracolonic aerodigestive cancer (e.g., cancer of the small intestine, gall bladder, bile duct, pancreas, liver, stomach, esophagus, or lung, or a naso-oropharyngeal cancer). It will be appreciated that the stool samples prepared as described herein can be used to detect a neoplasm marker in a mammal having a combination of different neoplasms. For example, the stool samples provided herein can be used to detect neoplasm-specific biomarkers in a human having lung and stomach neoplasms. The term "neoplasm" as used herein refers to any new and abnormal growth of tissue. Thus, a neoplasm can be a premalignant neoplasm or a malignant neoplasm.

As described herein, a stool sample can be prepared by reducing the level of any polypeptide that is common to stool. For example, a human stool sample can be prepared such the level of one or more (e.g., two, three, four, five, six, seven, eight, nine, ten, or more) polypeptides common to human stool from normal, healthy humans is reduced. The level of any such polypeptides can be reduced by 5, 10, 15, 20, 25, 30, 35, 40, 45, 50, 55, 60, 65, 70, 75, 80, 85, 90, 95, or more percent. In some cases, the level of a polypeptide common to human stool from normal, healthy humans can be reduced to a level below detection using IgY column depletion. For example, IgY antibodies can be raised against specific antigens, and a column can be generated with the raised antibodies conjugated to a support resin. In some cases, the methods and materials provided herein can be used to reduce the level of a polypeptide abundant in human stool. Examples of polypeptides that are abundant in human stool include, without limitation, the polypeptides listed in Table 1. Examples of polypeptides common to human stool from normal, healthy humans include, without limitation, the polypeptides listed in Tables 1, 2, and 3.

TABLE 1

Abundant polypeptides present in stool.

| Polypeptide | Accession No.* |
| --- | --- |
| Maltase Glucoamylase | MGA_HUMAN |
| IgGFc-binding protein | FCGBP_HUMAN |
| Alpha-1-antitrypsin | A1AT_HUMAN |
| Pancreatic alpha-amylase | AMYP_HUMAN |
| Serpin B6 | SPB6_HUMAN |
| Alpha-1-antichymotrypsin | AACT_HUMAN |
| Dipeptidyl peptidase 4 | DPP4_HUMAN |
| Elastase-2A precursor | ELA2A_HUMAN |
| Selenium-binding protein 1 | SBP1_HUMAN |
| Sucrase Isomaltase | SUIS_HUMAN |

*Accession numbers are from the Swissprot database.

Any appropriate method can be used to reduce the level of a polypeptide present within a stool sample. For example, IgY antibodies raised against specific antigens can be conjugated to a column resin and used to deplete high abundance polypeptides. Protein A or G columns can be used to deplete antibodies within a sample.

Once a stool sample having a reduced level of one or more polypeptides (e.g., abundant polypeptides) is obtained, any appropriate method can be used to assess the sample for a biomarker indicative of a disease such as cancer. For example, a stool sample provided herein can be used in assays designed to detect low abundance biomarkers indicative of disease. Appropriate methods such as those described elsewhere (Aebersold and Mann, *Nature*, 422:198-207 (2003) and McDonald and Yates, *Dis. Markers*, 18:99-105 (2002)) can be adapted or designed to detect polypeptides in a complex matrix. For example, single-reaction monitoring using a TSQ mass spectrometer can specifically target low abundance polypeptides in a complex matrix. High Resolution instruments like the LTQ-FT or LTQ orbitrap can be used to detect polypeptides present in a complex matrix.

The invention will be further described in the following examples, which do not limit the scope of the invention described in the claims.

EXAMPLES

Example 1

Soluble Proteome of Human Stool

Stool Preparation

Patients were recruited by study coordinators to participate in stool analysis studies. Samples were collected in a stool specimen container with instructions to pour a preservative buffer over the contents after defecation. Collection vessels were either mailed in or returned to the clinic and processed within 72 hours after collection. Upon arrival stools were homogenized in a Seward Stomacher, model 400 using a filter bag, Brinkman BA6041/STR 177×305 mm, for 60 seconds on normal setting. Homogenates were aliquoted and frozen at −70° C. Freezing lysed animal cells, but not bacteria. Protein extraction involved thawing and centrifuging samples at 5,311×g for 10 minutes and 10,733×g for 30 minutes. This procedure continued with a 10-minute microcentrifugation at 14,000 rpms and syringe filtration using a 0.45 µm filter. The syringe filter removed all debris and bacteria. Final preparation involved diluting samples 1:3 in PBS (Roche, cat#1666789). Total protein present in stool was quantitated using a Bradford Protein Assay kit (Pierce cat#500-0006).

1-Dimensional Electrophoresis

The total protein concentration of stool supernatants were determined by Bradford assay and samples were normalized based on the reading. Normalized samples were diluted 1:1 in Leammli-BME buffer and boiled for five minutes. Diluted samples (12 µL) were loaded onto BioRad Criterion 10.5-14% gradient gel and run for 50 minutes at 200 volts. All gels were stained in BioSafe Coomassie Stain (BioRad cat#161-0786) and destained in DI water. Six vertical slices were cut from 250 kDa to the bottom of the lane (FIG. 1), and the slices were digested using the methods described elsewhere (Wilm et al., *Nature*, 379:466-469 (1996)). Six vertical bands (0.2 cm×0.8 cm) were cut from each lane (FIG. 1) and cut into three 0.3×0.2 cm pieces, placed in PCR tubes, and rehydrated in 200 mM Tris pH 8.2 with a volume that covered the entire gel slice (100 µL). The gel slices were destained in 100 µL 50/50 acetonitrile/50 mM Tris pH 8.2 and then dehydrated in 100 µL 100% acetonitrile for 10 minutes. The gel slices were reduced in 100 µL of 30 µM DTT (in 20 mM Tris pH 8.2) and then the sulfhydryl groups were alkylated in 100 µL 50 µM iodoacetamide (in 20 mM Tris pH 8.2). Following dehydration in 100 µL 100% acetonitrile, the gel slices were digested for 12 hours at 37° C. in 80 µL 0.004 µg/µL trypsin (Promega sequencing grade V511A) dissolved in 20 mM Tris pH 8.2 containing Zwittergent 3-16 in 0.0002%, and the supernatant collected and saved. Gel slices were then extracted in 100 µL of 2% TFA and then in 100 µL 100% acetonitrile. The gel-slice digest was lyophilized using a Savant SPD121P Speedvac. Samples were lyophilized for four hours in a Savant Speedvac (Thermo Fisher Scientific Waltham, Mass. 02454) and reconstituted in 60 µL solvent (2% acetonitrile, 0.15% formic acid 0.05% trifluoroacetic acid, 0.0001% zwittergent 3-16) for MS analysis.

2-Dimensional Electrophoresis

Isoelectric focusing was performed using 11 cm, 3-10 non-linear pH gradient strips (BioRad ready-strip cat#163-2016) and rehydrated overnight. Stool supernatant containing ~50 µg protein was dissolved in 7 M Urea, 2 M thiourea, and 4% CHAPS (724 buffer) with 1% ampholytes 3-10 (BioRad cat#163-2094) applied to the strip and rehydrated overnight. Strips were washed three times for 10 minutes to remove bile and salts with 724 buffer. Strips were focused for 30,000 volt-hours at 8000 volts with a 50 µA maximum current. The second dimension was run using 10-14% precast Biorad Criterion gels run at 200 volts for 50 minutes. Gels were stained in Sypro Ruby (Invitrogen Corp. cat# S12000) overnight following fixing in methanol.

Mass Spectrometry

All vertical gel band digests were separated by nanoLC and analyzed using electrospray tandem mass spectrometry. Data acquisition was performed on a Finnigan LTQ Orbitrap hybrid mass spectrometer (Thermo-Fisher Waltham, Mass. 02454) with a nanospray ion source connected to an Eksigent nanoLC-2D pumping at 10 µL/minute. Binding was done using a 25 µL Optipak trap cartridge packed with 5 µm Magic C8 (Michrom Bioresources, Inc. Auburn, Calif. 95603) and chromatographic separation performed using a 75×200 C18 reverse phase column (Michrom Bioresources, Inc.).

Lyophilized samples were reconstituted in mobile phase A (0.15% TFA 0.05% FA), and 20 μL injected at 500 nL/minute with a 75 minute gradient from 5-90% with 98% acetonitrile. MS was done in data dependent mode to automatically switch between MS and MS2 acquisition on the three most abundant ions with an exclusion time window of 60 seconds. Survey scans were acquired with resolution of 60,000 at 400 m/z using FWHM with a target accumulation of 106 counts. An isolation width of 2.5 m/z was applied. Exclusion mass width was 0.6 m/z on low end and 1.5 m/z on high end. All acquisition and method development was performed using Xcaliber version 2.0.

Database Searching all ms/ms

Samples were analyzed using Mascot (Matrix Science, London, UK; version 2.1.03), Sequest (ThermoFinnigan, San Jose, Calif.; version 27, rev. 12) and X! Tandem (World Wide Web at "thegpm.org"; version 2006.09.15.3). Sequest was set up to search the "Sprot_20060905_human_nitro.fasta.hdr" database, which includes nitrotyrosine as a variable modification. Mascot was set up to search the "Sprot_20072905" database (selected for all taxa) assuming the digestion enzyme trypsin. X! Tandem was set up to search the "Sprot_20072905" database assuming the digestion enzyme trypsin. Mascot and X! Tandem were searched with a fragment ion mass tolerance of 0.80 Da and a parent ion tolerance of 10.0 PPM. Sequest was searched with a fragment ion mass tolerance of 1.00 Da. Nitration of tyrosine was specified in Mascot as a variable modification.

Criteria for Polypeptide Identification

Scaffold (version Scaffold-01_06_06, Proteome Software Inc., Portland, Oreg.) was used to validate MS/MS based polypeptide identifications. Peptide identifications were accepted if they could be established at greater than 95.0 percent probability as specified by the Peptide Prophet algorithm (Keller et al., Anal. Chem., 74(20):5383-92 (2002)). Protein identifications were accepted if they could be established at greater than 99.0 percent probability and contained at least two identified peptides. Protein probabilities were assigned by the Protein Prophet algorithm (Nesvizhskii, Anal. Chem., 75(17):4646-58 (2003)). Proteins that contained similar peptides and could not be differentiated based on MS/MS analysis alone were grouped to satisfy the principles of parsimony.

Determination of False Positive Rate

False positive rates were determined using a Swissprot reverse protein database. MS/MS data were searched using Mascot. Non-redundant protein IDs from the reverse database were determined using the following equation: $[(2 \cdot \Sigma F)/\Sigma T]100$ where F is the number of false positive hits, and T is total number of non-redundant proteins IDs.

Results

Figure 1:
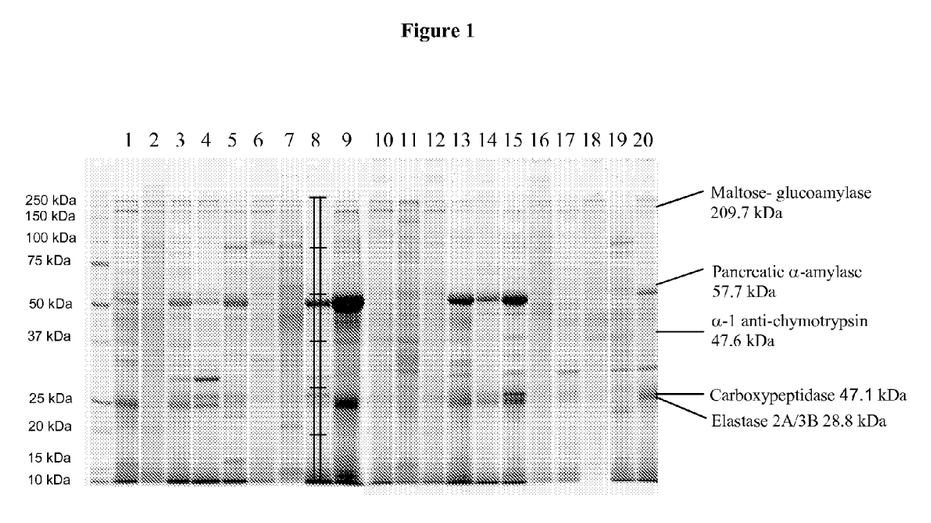
FIG. 1 is a photograph of 1-D BioSafe coomassie stained gel of stool supernatants from twenty patients with no history of digestive disease. The polypeptide identities of several bands from patient 20 are labeled.

To observe global similarities between patient samples and to achieve adequate reduction and denaturation, stool supernatants were electrophoretically separated prior to proteolytic digest. As an initial survey of the high-abundance polypeptides in stool, bands that were commonly present were excised and digested for polypeptides ID as shown in FIG. 1. Following this initial, global polypeptide study, a strategy for vertical GeLC gel slice excision was developed. Vertical bands were cut as shown in FIG. 1, and gel slices were digested in-gel and extracted using standard methods. 1-D PAGE for MS analysis separated a total of 20 patient samples with no history of digestive disease. The patient ages ranged from 30-50.

The Proteome of the Human Stool Supernatant

To gain insight into the high-abundance proteins of the aqueous phase of stool, an annotated list of commonly-present polypeptides from 20 different patient stool samples was generated. In total, the stool proteome list provides information for 63 unique polypeptides that were present in at least 50% of the samples and exhibited a spectral count of at least 3 observed spectra. Table 2 includes information that elucidates the quality of polypeptide IDs including percent coverage and the commonality of the polypeptides (out of 20 samples). For the set of polypeptides identified as being present in human stool supernatant, the majority were human in origin with the remainder consisting of bacterial and dietary polypeptides. The polypeptides listed in Table 2 are only the most common and abundant, and thus the list does not contain all polypeptides found in each sample. A typical stool sample contained roughly 100 identified polypeptides including human (83%), bacterial (15%), and dietary (2%) polypeptides.

TABLE 2

List of polypeptides comprising the proteome of stool.

| Polypeptide name | Accession number* | MW(kDa) | % Coverage | % Incidence | Spectral count |
|---|---|---|---|---|---|
| 1. Pancreatic alpha-amylase | AMYP_HUMAN | 57689.4 | 40% | 70% | 319 ± 80% |
| 2. Elastase-3A precursor | ELA3A_HUMAN | 29456.1 | 25% | 95% | 150 ± 50% |
| 3. Polymeric-immunoglobulin receptor precursor (Poly-Ig receptor) (PIGR) | PIGR_HUMAN | 83295.4 | 15% | 90% | 120 ± 37% |
| 4. Maltase-glucoamylase, intestinal | MGA_HUMAN | 209725.3 | 22% | 100% | 101 ± 21% |
| 5. IgGFc-binding protein | FCGBP_HUMAN | 572033.6 | 20% | 100% | 45 ± 33% |
| 6. Immunoglobulin components | see Table 3 | | | 100% | |
| 7. Alpha-1-antitrypsin | A1AT_HUMAN | 46719.9 | 25% | 100% | 144 ± 60% |
| 8. Elastase-3B precursor | ELA3B_HUMAN | 29274.7 | 42% | 85% | 65 ± 50% |
| 9. Elastase-2A precursor | ELA2A_HUMAN | 28869.3 | 40% | 85% | 60 ± 50% |
| 10. Dipeptidyl peptidase 4 | DPP4_HUMAN | 88263 | 30% | 80% | 52 ± 40% |
| 11. Salivary alpha-amylase | AMYS_HUMAN | 57750.4 | 15% | 50% | 50 ± 40% |
| 12. Carboxypeptidase A1 | CBPA1_HUMAN | 47123.6 | 31% | 90% | 40 ± 50% |
| 13. Carcinoembryonic antigen-related (CEA) | CEAM5_HUMAN | 76777.9 | 11% | 100% | 31 ± 45% |
| 14. Alpha-1-antichymotrypsin | AACT_HUMAN | 47653.0 | 26% | 100% | 34 ± 50% |
| 15. Mucin-2 precursor (Intestinal mucin-2) | MUC2_HUMAN | 540252.1 | 2% | 100% | 30 ± 45% |
| 16. Serpin B6 | SPB6_HUMAN | 42572.7 | 32% | 90% | 59 ± 33% |
| 17. Sucrase Isomaltase | SUIS_HUMAN | 209258.6 | 5% | 70% | 45 ± 40% |

TABLE 2-continued

List of polypeptides comprising the proteome of stool.

| Polypeptide name | Accession number* | MW(kDa) | % Coverage | % Incidence | Spectral count |
|---|---|---|---|---|---|
| 18. Intestinal alkaline phosphatase | PPBI_HUMAN | 56794.4 | 46% | 90% | 24 ± 80% |
| 19. Angiotensin-converting enzyme, somatic isoform | ACE_HUMAN | 149718 | 21% | 80% | 23 ± 40% |
| 20. Carboxypeptidase B | CBPB1_HUMAN | 47350.3 | 20% | 80% | 20 ± 200% |
| 21. Selenium-binding protein 1 | SBP1_HUMAN | 52295.7 | 17% | 85% | 20 ± 25% |
| 22. Phospholipase A2 | PA21B_HUMAN | 16360.1 | 57% | 85% | 14 ± 40% |
| 23. Protocadherin LKC | PCDLK_HUMAN | 141556.6 | 15% | 90% | 13 ± 45% |
| 24. Aminopeptidase N | AMPN_HUMAN | 109514.3 | 15% | 50% | 13 ± 40% |
| 25. Zymogen granule membrane protein 16 | ZG16_HUMAN | 18177.1 | 58% | 100% | 12 ± 40% |
| 26. Caldecrin precursor (Chymotrypsin C) | CLCR_HUMAN | 29465.5 | 40% | 95% | 12 ± 36% |
| 27. Trypsin-2 precursor | TRY2_HUMAN | 26470 | 16% | 40% | 12 ± 40% |
| 28. Enteropeptidase | ENTK_HUMAN | 112908.1 | 10% | 90% | 11 ± 90% |
| 29. Kallikrein-1 precursor | KLK1_HUMAN | 28870.8 | 15% | 85% | 10 ± 30% |
| 30. Alpha-amylase 2B | AMYC_HUMAN | 57692.3 | 68% | 85% | 8 ± 70% |
| 31. Antithrombin-III | ANT3_HUMAN | 52604.1 | 16% | 100% | 6 ± 60% |
| 32. N-acetylated-alpha-linked acidic dipeptidase-like protein | NALDL_HUMAN | 80623.3 | 10% | 80% | 6 ± 50% |
| 33. Alpha-1-acid glycoprotein 1 precursor (AGP 1) | A1AG1_HUMAN | 23494.1 | 30% | 90% | 5 ± 20% |
| 34. Carbonic anhydrase 1 | CAH1_HUMAN | 28721.2 | 52% | 50% | 4 ± 50% |
| 35. Protein S100-A9 | S10A9_HUMAN | 13242.3 | 13% | 90% | 5 ± 60% |
| 36. Protein S100-A8 | S10A8_HUMAN | 10835.0 | 15% | 80% | 5 ± 50% |
| 37. Transthyretin precursor | TTHY_HUMAN | 15868.9 | 25% | 60% | 15 ± 80% |
| 38. Xaa-Pro dipeptidase | PEPD_HUMAN | 55000 | 25% | 30% | 8 ± 30% |
| 39. Low-density lipoprotein receptor-related protein 1 | LRP1_HUMAN | 507121.2 | 2% | 85% | 4 ± 50% |
| 40. Zinc-alpha-2-Glycoprotein | ZA2G_HUMAN | 33854.1 | 15% | 85% | 6 ± 50% |
| 41. Leukocyte elastase inhibitor (LEI) (Serpin B1) | ILEU_HUMAN | 42763.8 | 13% | 100% | 7 ± 80% |
| 42. Zymogen granule membrane protein 16 | ZG16_HUMAN | 18177.1 | 40% | 50% | 6 ± 90% |
| 43. Neutrophil gelatinase-associated lipocalin precursor | NGAL_HUMAN | 22558.9 | 30% | 95% | 8 ± 30% |
| 44. CUB and zona pellucida-like domain-containing protein 1 precursor | CUZD_HUMAN | 68000 | 10% | 25% | 6 ± 50% |
| 45. Lithostathine 1 alpha | REG1A_HUMAN | 18731.0 | 31% | 50% | 5 ± 40% |
| 46. Kallikrein-1 precursor | KLK1_HUMAN | 28870.8 | 15% | 85% | 10 ± 30% |
| 47. Keratinocyte proline-rich protein | KPRP_HUMAN | 64000 | 10% | 50% | 4 ± 50% |
| 48. Meprin A subunit beta | MEP1B_HUMAN | 80000 | 7% | 60% | 11 ± 40% |
| 49. Hornerin (Human) | HORN_HUMAN | 282000 | 5% | 90% | 3 ± 33% |
| 50. Xaa-Pro aminopeptidase 2 | XXP2_HUMAN | 75625.4 | 17% | 80% | 3 ± 33% |
| 51. N-acetylated-alpha-linked acidic dipeptidase-like protein | NALDL_HUMAN | 80623.3 | 6% | 80% | 3 ± 33% |
| 52. Ectonucleotide pyrophosphatase/phosphodiesterase family member 7 | ENPP7_HUMAN | 51494.6 | 6% | 85% | 3 ± 33% |
| 53. Nucleophosmin (NPM) | NPM_HUMAN | 32575.5 | 14% | 80% | 3 ± 33% |
| 54. Antithrombin-III | ANT3_HUMAN | 52604.1 | 8% | 80% | 3 ± 33% |
| 55. Galectin-4 | LEG4_HUMAN | 36 kDa | 12% | 80% | 3 ± 33% |
| 56. Galectin-3-binding protein | LG3BP_HUMAN | 65332.1 | 5% | 60% | 3 ± 33% |
| 57. Pancreatic triacylglycerol lipase | LIPP_HUMAN | 51157.1 | 6% | 70% | 3 ± 33% |
| 58. Epithelial-cadherin | CADH1_HUMAN | 97000 | 10% | 50% | 3 ± 33% |
| 59. Mucin and cadherin-like Protein | MUCDL_HUMAN | 88000 | 15% | 50% | 3 ± 33% |
| Bacterial proteins *Escherichia coli* | | | | | |
| 60. Thioredoxin 1 | THIO_ECO57 | 12000 | 30% | 85% | 4 ± 50% |
| *Bacteroides thetaomicorn* | | | | | |
| 61. Phosphoenolpyruvate Carboxykinase | PPCK_BACTN | 59164.9 | 14% | 75% | 3 ± 33% |
| 62. Uronate isomerase | UXAC_BACTN | 56318.7 | 27% | 65% | 12 ± 40% |
| 63. Xylose isomerase | XYLA_BACTN | 48939.8 | 21% | 80% | 16 ± 50% |
| 64. Glutamate dehydrogenase | DHE3_BACTN | 49017.7 | 9% | 60% | 3 ± 33% |

TABLE 2-continued

List of polypeptides comprising the proteome of stool.

| Polypeptide name | Accession number* | MW(kDa) | % Coverage | % Incidence | Spectral count |
|---|---|---|---|---|---|
| 65. Hydroxylamine reductase | HCP_BACTIN *Bacteroides fragilis* | 59841.5 | 8% | 65% | 4 ± 50% |
| 66. NAD-specific glutamate dehydrogenase | DHE3_BACFR | 48391.5 | 24% | 70% | 8 ± 50% |
| 67. Phosphoenolpyruvate carboxykinase | PPCK_BACFN | 59000 | 15% | 100% | 3 ± 33% |

*Accession numbers are from the Swissprot database.

TABLE 3

Immunoglobulin components present within stool.

| Polypeptide name | Accession numbers* | Molecular Weight (AMU) | Spectral count |
|---|---|---|---|
| IgGFc-binding protein | FCGBP_HUMAN | 572015.6 | 346 |
| Ig kappa chain C region | KAC_HUMAN | 11590.5 | 82 |
| Ig alpha-1 chain C region | IGHA1_HUMAN | 37635.8 | 57 |
| Ig lambda chain C regions | LAC_HUMAN | 11218.1 | 19 |
| Epithelial-cadherin | CADH1_HUMAN | 97439.6 | 8 |
| Immunoglobulin J chain | IGJ_HUMAN | 15576.5 | 18 |
| Ig kappa chain V-III region SIE | KV302_HUMAN KV305_HUMAN | 11757.4 | 14 |
| Ig gamma-1 chain C region | IGHG1_HUMAN | 36087 | 11 |
| Ig alpha-1 chain C region | IGHA1_HUMAN | 37736.7 | 6 |
| Ig heavy chain V-III region CAM | HV307_HUMAN | 13645.2 | 9 |
| Ig lambda chain V-III region LOI | LV302_HUMAN | 11916.9 | 3 |
| Ig heavy chain V-III region TUR | HV318_HUMAN | 12412 | 5 |
| HLA class II histocompatibility antigen | 2DRA_HUMAN 2DRA_MACMU | 28589.1 | 2 |
| Ig heavy chain V-III region KOL | HV311_HUMAN | 13700 | 4 |
| Ig kappa chain V-I region EU | KV106_HUMAN | 11770.5 | 7 |
| Ig gamma-2 chain C region | IGHG2_HUMAN IGHG4_HUMAN | 35865.2 | 4 |
| Ig heavy chain V-II region ARH-77 | HV209_HUMAN | 16210.6 | 9 |
| Ig heavy chain V-III region TRO | HV301_HUMAN | 13448.2 | 3 |
| Ig kappa chain V-II region TEW | KV204_HUMAN | 12297.3 | 8 |
| Ig kappa chain V-IV region | KV401_HUMAN KV403_HUMAN | 13362.3 | 2 |
| Ig mu chain C region | MUC_HUMAN | 49537.9 | 7 |
| Ig lambda chain V-I region HA | LV102_HUMAN | 11878.1 | 4 |

*Accession numbers are from the Swissprot database.

Each vertical gel slice contained an average of 25 polypeptides using a composite identification from Mascot, Sequest, and Xtandem. This number of polypeptide IDs increased, on average, from 15 IDs in the top most gel slice (100-250 kDa) to 45 in the lowest gel slice (<10-20 kDa). The polypeptides were identified with a false positive rate of 6.8 on average from all 20 samples. The proteome contained 63 consistently expressed polypeptides, which are listed in Table 2 according to spectral count calculated using Scaffold (number of identified spectra) (Proteome Software Inc.).

Distribution of Polypeptides

Figure 2:
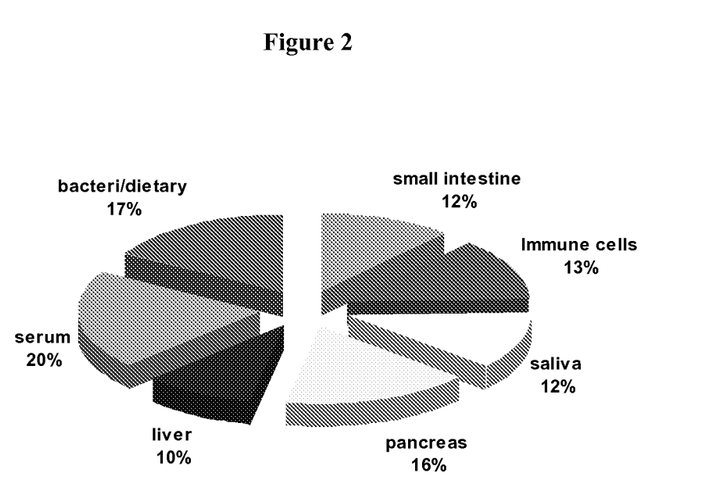
FIG. 2 is a pie diagram of the anatomic origins of polypeptides found in stool. Polypeptides obtained from stool were divided into groups based on their anatomic origin, and the percentage of the whole for each representative group was determined. The "other" category includes bacterial and dietary polypeptides.

The polypeptides of stool supernatant were distributed among several organ locations, primarily of digestive function originating from saliva, pancreatic juice, and the small intestine (FIG. 2). The remaining polypeptides were from serum, liver, and non-human sources. Several polypeptides were abundant in multiple gel slices, though sequence coverage was greatest in the vertical gel slice that contained the full length polypeptide.

Only 15% of the polypeptides present in each sample were bacterial. Polypeptides from bacterial genus *Bacteroides* and from species *Escherichia coli* were commonly present in varying abundance (3-16 unique peptides). Though there was significant variation in the type and abundance of these polypeptides, there were nine bacterial polypeptides that were commonly present in the samples. Table 2 lists those polypeptides that were present in most of the samples, though this is not a complete list of all the polypeptides that were observed.

Additionally, there were several dietary polypeptides present in the samples. Common dietary polypeptides included those from *Gallus gallus* (chicken), *Bos taurus* (cow), *Malus x domestica* (apple), and *Triticum aestivum* (wheat). All polypeptides in the list in Table 2 met criteria for proper ID, including the presence of at least 3 unique and confirmed spectra.

Figure 3:
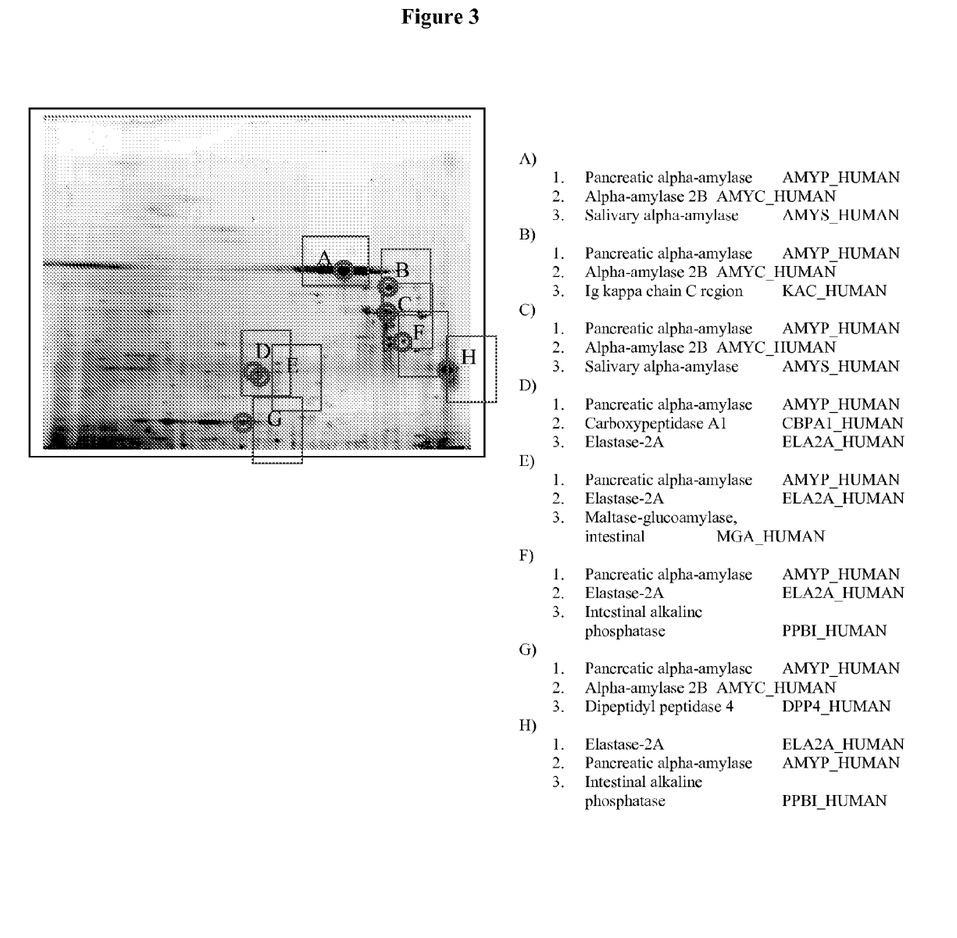
FIG. 3. Spot identification for eight spots from 2-DE gel $A_2$. The identified spots are marked with a circles and the top three polypeptide IDs (>20 total spectra) for each spot are listed.

To further corroborate the polypeptide IDs, spots were cut from 2-dimensional gels and identified. FIG. 3 shows individual spots and their top three IDs. The prominent spots and their IDs match the higher abundance polypeptides from Table 2. All of the observed polypeptides from the 2-DE gels were in the top twenty polypeptides from Table 2.

Intrapatient Similarity of Stool Samples

2-DE was used to analyze samples from four different patients for comparison of consistent polypeptide expression.

Intrapatient Similarity

Figure 4:
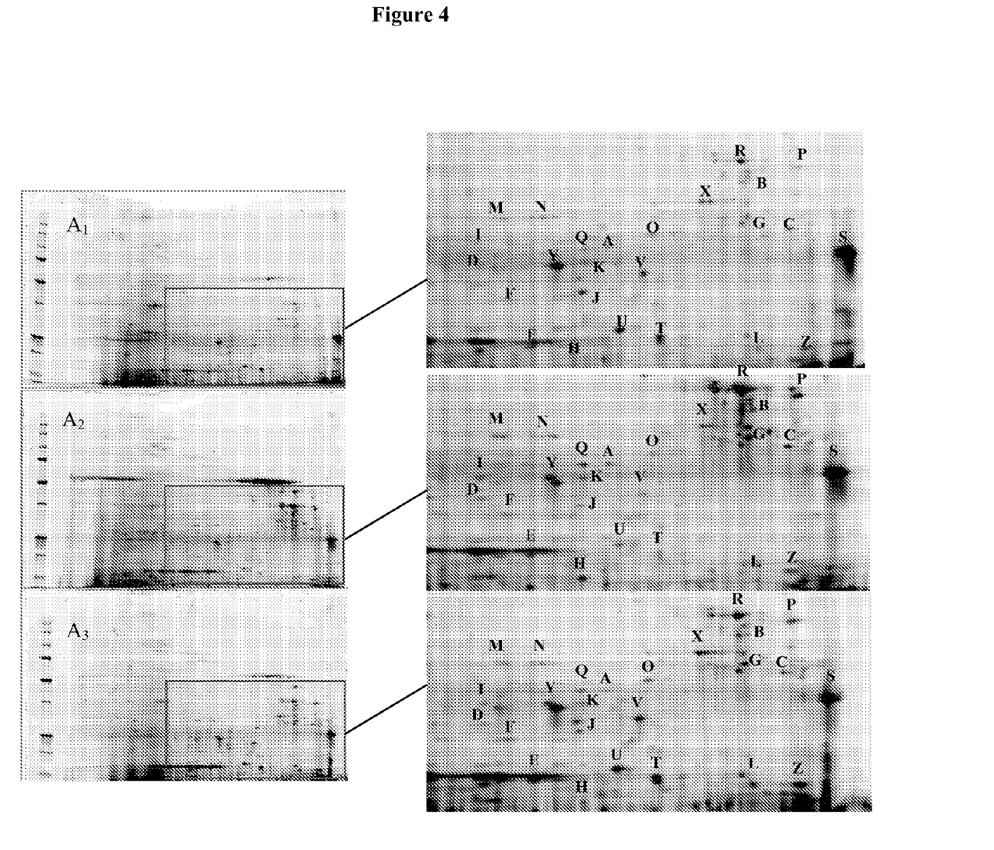
FIG. 4. 2-DE gels for three samples from a single patient over one week. The yellow box is expanded to show regions of similarity which are marked for comparison. The white dots correspond to specific landmarks used in similarity score determination. Similarity scores of 40% and 39% were calculated for gels $A_1$ and $A_3$ respectively in reference to gel $A_2$.
Figure 5:
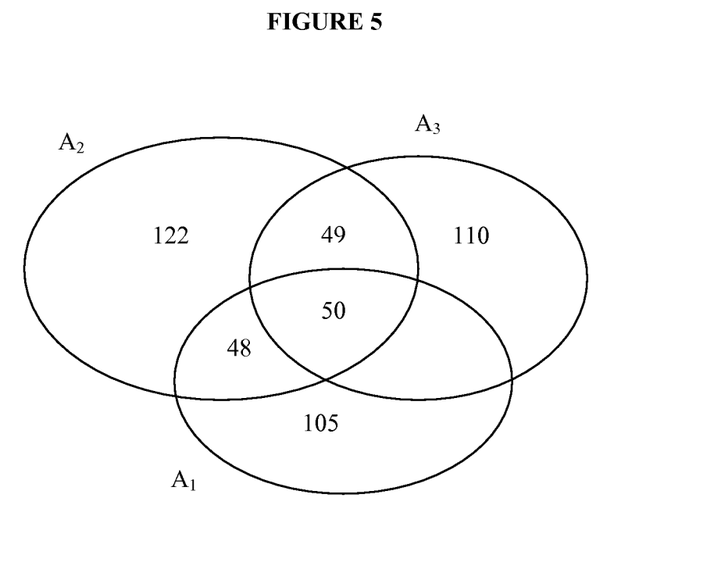
FIG. 5 is a Venn diagram of spot similarity for three samples from a single patient.

Following the compilation of the human proteome, intrapatient variability was determined by analyzing three samples from the same patient over a week. Samples were separated by 2-dimensional electrophoresis including a post-rehydration desalting method described elsewhere (Heppelmann et al., *Electrophoresis*, 28(21):3988-91 (2007)) to remove bile salts from the samples. Using PDQuest software (BioRad version 7.4.0) to match 2-D gel spots, an intrapatient similarity scores of 40% and 39% for the three gels was calculated with 105, 122, and 110 spots picked for gels $A_1$, $A_2$, and $A_3$, respectively (FIGS. 4 and 5). 50 spots matched between all three gels (FIG. 5). All three gels were matched to sample $A_2$, and regions of similarity and landmark spots were utilized in spot matching (FIG. 4).

Interpatient Similarity

Another component to identifying the stool proteome was assessing the variability between different patient samples. The top twenty (with the exception of pancreatic alpha amylase AMYP_HUMAN) were present in at least 16 of the twenty samples. Standard deviations for spectral counts ranged from 20%-200%, with a mean deviation of 46% between samples. The total variance (using the deviation score method) was 54%. This was due, in part, to the fact that total-polypeptide concentration of stool is difficult to measure by spectrophotometric methods because bile contaminants are not easily removed.

Example 2

Depleting Polypeptides from Stool

A depletion column with a capture resin is constructed to remove high abundance polypeptides. The capture resin is designed to contain IgY antibodies (Genway; San Diego, Calif.) raised against specific abundant polypeptides. The IgY columns are similar to those used to deplete polypeptides from serum.

In some cases, a physical depletion strategy can include affinity chromatography (e.g., antibody depletion), ion exchange depletion, and protein depletion using dye-conjugated resins (like cibacron blue for albumin). Standard products are available for serum depletion including (1) the Agilent (Santa Clara, Calif.) Multiple Affinity Removal System (MARS), which uses several antibodies specific to high-abundance human proteins in serum, (2) the Qiagen (Valencia, Calif.) albumin/IgG depletion cartridges, which specifically targets human IgG and albumin, and (3) the proteospin (Norgen Biotek, St. Catharines, ONT, Canada), which uses an ion exchange resin to deplete albumin, a-antitrypsin, and haptoglobin. Genway IgY columns (Genway Biotech, Inc. San Diego, Calif.) can be custom build to a customer's specifications or a pre-made column designed to deplete a standard list of proteins can be obtained commercially. Lower abundance polypeptide can be enhanced by electrophoretically separating the sample on a 1-dimensional or 2-dimensional polyacrylamide gel and isolating bands or spots for digestion. A last step for simplifying matrix complexity can include separation by reverse-phase chromatography prior to spraying the sample into the source of a mass spectrometer. Retention time of the column can be a feature in the analysis of polypeptides.

Computational methods for reducing complexity of matrices can take place during data acquisition. High-abundance parent ions can be excluded as part of an ion exclusion list or a signal saturation level can be designated for high-abundance parent ions. This can allow lower abundance, co-eluting polypeptides to trigger ms/ms and be analyzed. This can be a standard part of most instrument methods for data dependent acquisitions. The following is a list of references related to mass spectrometry methods and matrix depletion strategies that can be used as described herein (Adkins et al., *Mol. Cell. Proteomics*, 1:947-955 (2002); Aebersold and Mann, *Nature*, 422:198-207 (2003); Björhall et al., *Proteomics*, 5:1: 307-317 (2004); Kelleher et al., *J. Am. Chem. Soc.*, 121:806-812 (1999); McDonald and Yates, *Dis. Markers*, 18:99-105 (2002); Merrell et al., *J. Biomol. Tech.*, 15:238-248 (2004); Tissot, *Proteomics*, 5:3019-3034 (2005); Richter et al., *J. Chromatogr. B Biomed. Sci. Appl.*, 726:25-35 (1999); Wolters et al., Anal. Chem., 73:5683-5690 (2001); and Wu et al., *J. Proteome Res.*, 2(4):383-93 (2003)).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for preparing a human stool sample for detecting polypeptide,
   wherein said method comprises reducing the concentration of two or more polypeptides known to be in high abundance within a human stool sample, wherein said two or more polypeptides are selected from the group consisting of pancreatic alpha-amylase, alpha-amylase 2B, salivary alpha-amylase, Ig kappa chain C region, carboxypeptidase A1, elastase-2A, maltase-glucoamylase intestinal, intestinal alkaline phosphatase, and dipeptidyl peptidase,
   wherein an antibody conjugated resin is used to reduce the concentration of pancreatic alpha-amylase, alpha-amylase 2B, salivary alpha-amylase, Ig kappa chain C region, carboxypeptidase A1, elastase-2A, maltase-glucoamylase intestinal, intestinal alkaline phosphatase, and dipeptidyl peptidase 4.

2. The method of claim 1, wherein said antibody is an IgY antibody.

* * * * *